(12) United States Patent
Thomas, Jr.

(10) Patent No.: US 9,820,510 B2
(45) Date of Patent: Nov. 21, 2017

(54) VAPOR DELIVERY DEVICE

(71) Applicant: Robert P Thomas, Jr., Phoenix, AZ (US)

(72) Inventor: Robert P Thomas, Jr., Phoenix, AZ (US)

( * ) Notice: Subject to any disclaimer, the term of this patent is extended or adjusted under 35 U.S.C. 154(b) by 364 days.

(21) Appl. No.: 14/588,932

(22) Filed: Jan. 3, 2015

(65) Prior Publication Data

US 2016/0295919 A1    Oct. 13, 2016

Related U.S. Application Data

(60) Provisional application No. 61/923,611, filed on Jan. 3, 2014.

(51) Int. Cl.
| | | |
|---|---|---|
| *A24F 47/00* | (2006.01) |
| *A61M 11/04* | (2006.01) |
| *A61M 15/00* | (2006.01) |

(52) U.S. Cl.
CPC ......... *A24F 47/008* (2013.01); *A61M 11/042* (2014.02); *A61M 15/00* (2013.01); *A61M 2205/3368* (2013.01); *A61M 2205/584* (2013.01); *A61M 2205/587* (2013.01); *A61M 2205/8206* (2013.01); *A61M 2205/8262* (2013.01)

(58) Field of Classification Search
CPC ..... A24F 47/008; A61M 11/042; A61M 15/00
See application file for complete search history.

(56) References Cited

U.S. PATENT DOCUMENTS

| | | |
|---|---|---|
| 3,200,819 A | 8/1965 | Gilbert |
| 4,141,369 A | 2/1979 | Burruss |
| 4,190,046 A | 2/1980 | Virag |
| 4,303,083 A | 12/1981 | Burruss, Jr. |
| 4,945,929 A | 8/1990 | Egilmex et al. |
| 4,947,875 A | 8/1990 | Brooks et al. |
| 4,993,435 A | 2/1991 | McCann |
| 5,249,586 A | 10/1993 | Morgan et al. |
| 5,456,269 A | 10/1995 | Kollasch |
| 5,819,756 A | 10/1998 | Mielordt |
| 5,865,185 A | 2/1999 | Collins et al. |

(Continued)

FOREIGN PATENT DOCUMENTS

| | | |
|---|---|---|
| EP | 2756860 A1 | 7/2014 |
| EP | 2862457 A1 | 4/2015 |

*Primary Examiner* — Ruth Ilan
(74) *Attorney, Agent, or Firm* — Invention To Patent Services; Alex Hobson

(57) ABSTRACT

A vapor delivery device for the delivery of a dose of vaporizable material includes a detachable dose cartridge having an oven. The oven is configured to contain a vaporizable material and at least oven vent configured to allow the flow of the vapor to a delivery port. The oven may be detachably attached to the dose cartridge. A detachable dose cartridge or oven may be sealed and have a dose of vaporizable material that is inaccessible inside. The vapor delivery device may accommodate organic, resin, prepackaged or liquid vaporizable materials. The oven vent or vents are configured to be either blocked or covered to substantially eliminate vapor escaping from the oven chamber. An oven chamber or oven closure, may be configured to rotate to trap vapor within the oven. In another embodiment, an oven is configured with a plunger that traps vapor within the oven.

14 Claims, 13 Drawing Sheets

(56) References Cited

U.S. PATENT DOCUMENTS

| | | |
|---|---|---|
| 5,915,387 A | 6/1999 | Baggett, Jr. et al. |
| 6,164,287 A | 12/2000 | White |
| 7,100,420 B2 | 9/2006 | Read et al. |
| 7,530,357 B2 | 5/2009 | Edwards, Jr. |
| 8,079,371 B2 | 12/2011 | Brewer, Jr. et al. |
| 8,205,622 B2 | 6/2012 | Pan et al. |
| 8,210,570 B1 | 7/2012 | Nagle |
| 8,490,628 B2 | 7/2013 | Hon |
| 8,550,068 B2 | 10/2013 | Minskoff et al. |
| 8,578,942 B2 | 11/2013 | Schennum |
| 8,603,397 B2 | 12/2013 | Baize et al. |
| 8,813,758 B2 | 8/2014 | Braveman |
| 8,897,628 B2 | 11/2014 | Conley et al. |
| 8,903,228 B2 | 12/2014 | Bartkowski et al. |
| 9,022,026 B2 | 5/2015 | Fang et al. |
| 2004/0177674 A1 | 9/2004 | Warren et al. |
| 2004/0187879 A1 | 9/2004 | Iordan |
| 2005/0016550 A1 | 1/2005 | Katase |
| 2008/0023001 A1 | 1/2008 | Watanabe |
| 2008/0072917 A1 | 3/2008 | Lee |
| 2008/0247892 A1 | 10/2008 | Kawasumi |
| 2009/0293892 A1* | 12/2009 | Williams .............. A24F 47/008 131/328 |
| 2010/0200008 A1 | 8/2010 | Taieb |
| 2010/0313901 A1 | 12/2010 | Chemla et al. |
| 2011/0192399 A1* | 8/2011 | Wilke .................. A61M 11/041 128/203.27 |
| 2011/0290269 A1 | 12/2011 | Shimizu |
| 2012/0118301 A1 | 5/2012 | Montaser |
| 2013/0192623 A1 | 8/2013 | Tucker et al. |
| 2014/0166028 A1 | 6/2014 | Fuisz et al. |
| 2014/0190478 A1 | 7/2014 | Liu |
| 2014/0196736 A1 | 7/2014 | Cordey et al. |
| 2014/0209110 A1 | 7/2014 | Han et al. |
| 2014/0283859 A1 | 9/2014 | Minskoff et al. |
| 2014/0305450 A1 | 10/2014 | Xiang |
| 2014/0318557 A1 | 10/2014 | Bremer |
| 2014/0318560 A1 | 10/2014 | Khon et al. |
| 2014/0334802 A1 | 11/2014 | Dubief |
| 2014/0366898 A1 | 12/2014 | Monsees et al. |
| 2015/0013704 A1 | 1/2015 | Maglione |
| 2015/0053219 A1 | 2/2015 | Roudier et al. |
| 2015/0083147 A1 | 3/2015 | Carrick et al. |
| 2015/0101625 A1 | 4/2015 | Brown et al. |

* cited by examiner

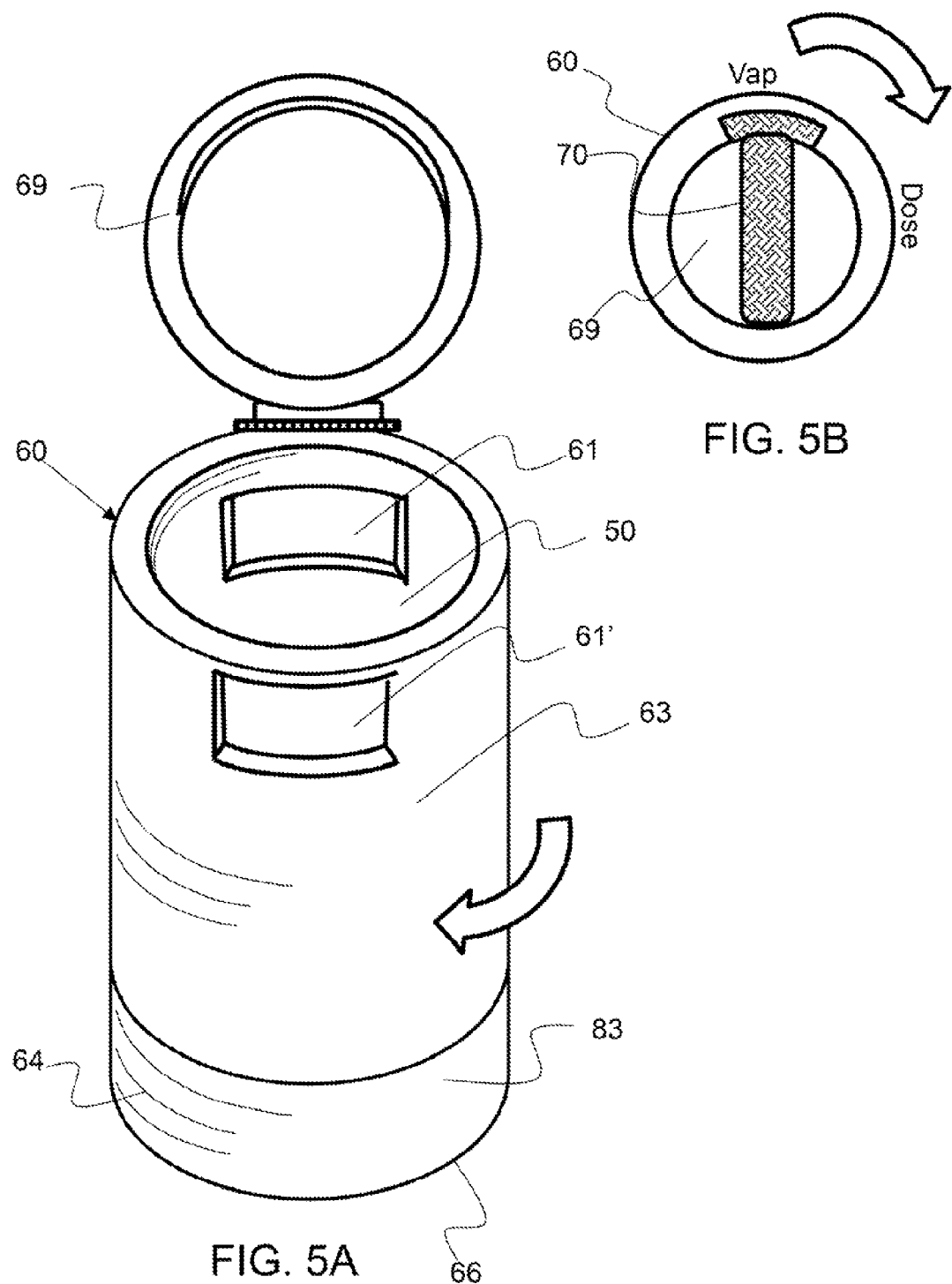

VAPOR DELIVERY DEVICE

CROSS-REFERENCE TO RELATED APPLICATIONS

This application claims the benefit of U.S. provisional patent application No. 61,923,611, filed on Jan. 3, 2014 and entitled Vapor Delivery Device; the entirety of which is incorporated by reference herein.

BACKGROUND OF THE INVENTION

Field of the Invention

The present invention relates to a device configured to provide a dose of vapor by heating a vaporizable material.

Background

Vaporizers used to produce a vapor for medicinal purposes are becoming more common as vaporizing materials significantly reduce the amount of carcinogenic smoke that is produced through conventional burning methods. A number of portable vaporizers are available, however they all have significant drawbacks. Most vaporizers are configured to only accept a certain type of vaporizable material, such as organic material or resin, but not liquids. The receptacle for receiving vaporizable materials is typically much larger than what is required for a dose of vaporizable material. Therefore, vaporizers do not efficiently heat the vaporizable material, as there is a large volume of empty space around the vaporizable material that consumes heat. This inefficient heating of the vaporizable material requires longer heating time to produce a dose of vapor. A user may sometimes have to wait as long as 5 minutes before a dose is ready. In addition, inefficient heating causes vaporizers to utilize a significant amount of power to heat the vaporizable material and therefore the battery life is quickly diminished. In addition, medicinal vaporizable doses having a specific size and geometry and in some cases being tamper proof, may become more prevalent. Current vaporizers are not configured to accept and efficiently vaporize these prepackaged doses. Vaporizers contain a heating element that is configured within the device and therefore may not be in as close proximity to the vaporizable material as possible.

There exists a need, for a vaporizing device that can accept all types of vaporizable material, more effectively and efficiently heats the vaporizable material and is configured to accept a prepackaged dose.

SUMMARY OF THE INVENTION

The invention is directed to a vapor delivery device for the delivery of a dose of vaporizable material. The vapor delivery device comprises a detachable dose cartridge that comprises an oven configured to contain a vaporizable material and air flow vents to allow flow of the vapor to a delivery port. In an exemplary embodiment, the oven comprises a heating element that draws power from heating element contact on the detachable dose cartridge. A user can load a vaporizable material into the oven chamber and attach the detachable dose cartridge to the cartridge port. The user can then start the heating process and when a vapor is produced, the user can open the one oven vent and receive a dose of vapor through the delivery port. In an exemplary embodiment, a user can set a heating temperature, such as high, medium or low, and when the vaporizable material has been exposed to an effective temperature for an effective amount of time, a ready indicator light may turn on, or flash to indicate that the dose is ready. The user may then turn the oven to align the oven vents with inlet and outlet airflow conduits and receive the dose.

A vapor delivery device comprises a controller that controls the functions of the device including, but not limited to, delivering electrical power from a power supply to a heating element, and receiving temperature feedback from a temperature sensor and controlling the ready indicator. A controller may be a microprocessor or a control circuit, for example. As described, a vapor delivery device may comprise a heat selector to select a general range of temperature, high, medium or low, for example, or an actual temperature. In another embodiment, material type selector may allow a user to select what type of material is being inserted into the oven, including an organic material, a resin, a liquid, or a prepackaged dose, for example. These different types of vaporizable materials may require different temperatures and/or durations of heating to produce an effective dose.

A vaporizable material may be any suitable type of material that can be vaporized to produce a dose of vapor for a user. In an exemplary embodiment, the material comprises tetrahydrocannabinol (THC) or cannabidiol (CBD), and the like. Cannabis and other materials may be vaporized in an organic form, as a concentrated resin or liquid, or in a prepackaged form. A prepackaged vaporizable material may be configured in a geometric shape conducive for placement in the oven, as described herein, and heated. For example, a prepackaged vaporizable material may be provided in a thin disc or puck shape that slides down into a cylindrical oven chamber. The thin puck may be quickly and efficiently heated by a heating element configured to deliver heat through the bottom of the oven chamber, for example. In another embodiment, a prepackaged vaporizable material comprises a cover that is thermally degraded to expose the vaporizable material when placed in an oven and heated.

A ready indicator may be a light that illuminates a first color when the vaporizable material is being heated and then changes color when the dose is ready, such as from red to green in color. In another embodiment, the ready indicator may illuminate when the vaporizable material is being heated and then flash when the dose is ready.

A temperature sensor may be configured to measure the temperature of the interior of the oven, the exterior of the oven or any other suitable part of the vapor delivery device or detachable cartridge that will correlate with an effective temperature of the vaporizable material. The temperature sensor may be coupled to the detachable cartridge or be part of the vapor delivery device body.

In an exemplary embodiment, electrical power is transferred from the power supply to the heating element through power supply contacts that electrically couple with heating element contacts. These contacts may be simply electrically conductive contact points or may comprise pins, plugs, sockets and the like. A power supply may be a battery or batteries configured in the vapor delivery device body or detachable cartridge, for example, or it may be a plug in power supply. A vapor delivery device may comprise a detachable electrical cord that may also be used to charge rechargeable batteries through a charging port. In another embodiment, a vapor delivery device comprises an electrical power cord and a separate charging port.

A heating element may be configured on the detachable cartridge, on the oven or on the vapor delivery device body. In an exemplary embodiment, the heating element is configured in the base of the oven, whereby it is in close proximity to the vaporizable material within the oven. In another embodiment, the heating element is configured within a portion of the interior surface of the oven, whereby it makes direct contact with the vaporizable material. In yet another embodiment, a heating element is configured on the detachable cartridge and a detachable oven is configured to couple with the heater when it is inserted into the detachable cartridge. Any suitable configuration or combination of configurations of the heater may be used. A vapor delivery device may comprise one, two, three or more heating elements.

A heating element may be a traditional resistive wire heater, heater cartridge or a flexible heating element. A flexible heating element comprises a resistive wire or film within a high temperature polymer cover, such as polyimide. When the heating element is located in close proximity, the temperatures achieved by a flexible heating element may be effective to produce a dose of vapor.

A detachable dose cartridge is configured to be coupled with a cartridge port. A detachable dose cartridge may be configured to slide into a cartridge port aperture, or snap into a cartridge port of the vapor delivery device. Any suitable way of coupling the charging port to the vapor delivery device body may be utilized. A detachable dose cartridge comprises inlet and outlet airflow conduits that are configured to align with one or more oven vents. In addition, the outlet airflow conduit is configured to align with a vapor conduit that leads to the delivery port. The term align, as used herein in reference to airflow vents and conduits, means that they align to allow vapor and/or airflow to pass from one to another. A delivery port may be configured with a mouthpiece and this mouthpiece may be configured to rotate into and away from the vapor delivery device body, pull out from the vapor delivery device body, and the like. A detachable dose cartridge may be any suitable shape including rectangular, round, polygonal, square, and the like.

An oven, as described herein, comprises at least one oven vent to allow the release of the vapor from the oven chamber, or interior of the oven. In an exemplary embodiment, an oven comprises a first oven vent that is configured to align with the inlet airflow conduit and a second oven vent configured to align with an outlet airflow conduit. This configuration allows for a cross-flow through the oven chamber to draw the vapor from the oven and air from outside of the vapor delivery device. An oven may comprise an oven closure that is configured to seal an oven access opening. An oven closure may be a lid that can be placed over the top of the oven and this lid may be hinged or otherwise attached. In another embodiment, the oven closure is detachable from the oven. An oven closure may comprise an oven closure lever that allows the oven to be spun or rotated within the detachable dose cartridge. The oven may be rotated to seal off the oven vents from the airflow conduits during a heating cycle and then rotated to align the oven vents with the airflow conduits when the heating cycle is complete, thereby allowing for the dispensing of the vapor dose. An oven closer lever may rotate the oven closure, or may be configured to spin the entire oven. In one embodiment, an oven closure lever is coupled to an oven closure having an oven closure vent opening(s) and rotation of the oven closure within the oven can align or misalign the oven closure vent opening(s) with the oven vent(s). In effect, the oven closure, or lid, may act as a damper to the oven vents. This type of oven closure may comprise an oven closure lever and a tab that is configured to facilitate alignment of the oven closure with the proper positions within the oven. The oven may comprise a tab receiver and labels to further facilitate proper function of the oven closure damper process.

An oven may comprise an oven lever or damper lever that extends from any portion of the oven to allow for rotation of the oven within the detachable dose cartridge, or rotation of a damper, respectively. An oven lever may extend from the top of the oven, where it may be exposed, or from the side of the oven. A detachable dose cartridge may comprise a manipulator slot that is configured to allow access to an oven lever and/or damper lever.

An oven may comprise a plunger, whereby the plunger may be inserted at least partially into the oven interior. A plunger may be configured to be inserted all the way down into the oven to compress or lay on a vaporizable material. This configuration may increase heating efficiency of the vaporizable material by reducing empty air volume within the interior of the oven chamber. The vapor volume of an oven chamber may be adjustable by adjusting the position of the plunger within the over, wherein when the plunger is pushed down against or close to the vaporizable material, the vapor volume of the interior volume of the oven is less than when the plunger is in a more retracted position from the vaporizable material. A plunger may act as an oven closure and may also prevent the release of vapor from the oven vents. A plunger may be configured to be inserted down past the oven vent(s). A plunger may be removed or released when the vaporizable material has been heated to an effective temperature. A vapor may then quickly fill the interior of the oven and be delivered to a user through a deliver port. In another embodiment, an oven comprises a plunger and an oven vent damper, whereby after the plunger is released, the oven vent damper must be rotated to allow the vapor to be released. In this way, the vaporizable material may be heated, then a vapor may be formed and then this vapor may be subsequently released.

An oven vent cover or damper is any configuration that cause the oven vent to not be exposed to the inlet and/or outlet airflow conduits. An oven vent cover may be a portion of an oven closure that is spun to block the oven vents, or it may be the oven being turned within a housing within the detachable dose cartridge, whereby the oven vents are not aligned with the airflow conduits, for example.

An oven may be configured as a sealed oven for a vaporizable material dose, whereby the dose of vaporizable material cannot be removed from the oven chamber, except as a vapor upon heating. A sealed oven may comprise a dose of vaporizable material that is attached to the oven interior and one or more oven vents.

The present invention provides a method of providing a dose of vapor from a vaporizable material comprising these steps: providing a vapor delivery device as described herein; placing a vaporizable material in an oven chamber; attaching the oven closure over the oven access opening; rotating a closure lever to turn the oven to a vaporize position, wherein the oven vents are not aligned with the inlet or outlet airflow conduits; activating the vapor delivery device to provide power to the heating element to heat and produce a vapor from the vaporizable material; rotating the oven closure lever to align the oven vents with the inlet and outlet airflow conduits; and inhaling to draw in the vapor from the oven to provide a dose of vapor to a user. It is to be noted that any suitable means, as described herein, to misalign and effectively seal the interior volume of the oven chamber, may be used during the vaporization process in place of the method described in the method above.

The summary of the invention is provided as a general introduction to some of the embodiments of the invention, and is not intended to be limiting. Additional example embodiments including variations and alternative configurations of the invention are provided herein.

BRIEF DESCRIPTION OF THE DRAWINGS

The accompanying drawings are included to provide a further understanding of the invention and are incorporated in and constitute a part of his specification, illustrate embodiments of the invention, and together with the description serve to explain the principles of the invention.

DETAILED DESCRIPTION OF THE ILLUSTRATED EMBODIMENTS

Figure 1:
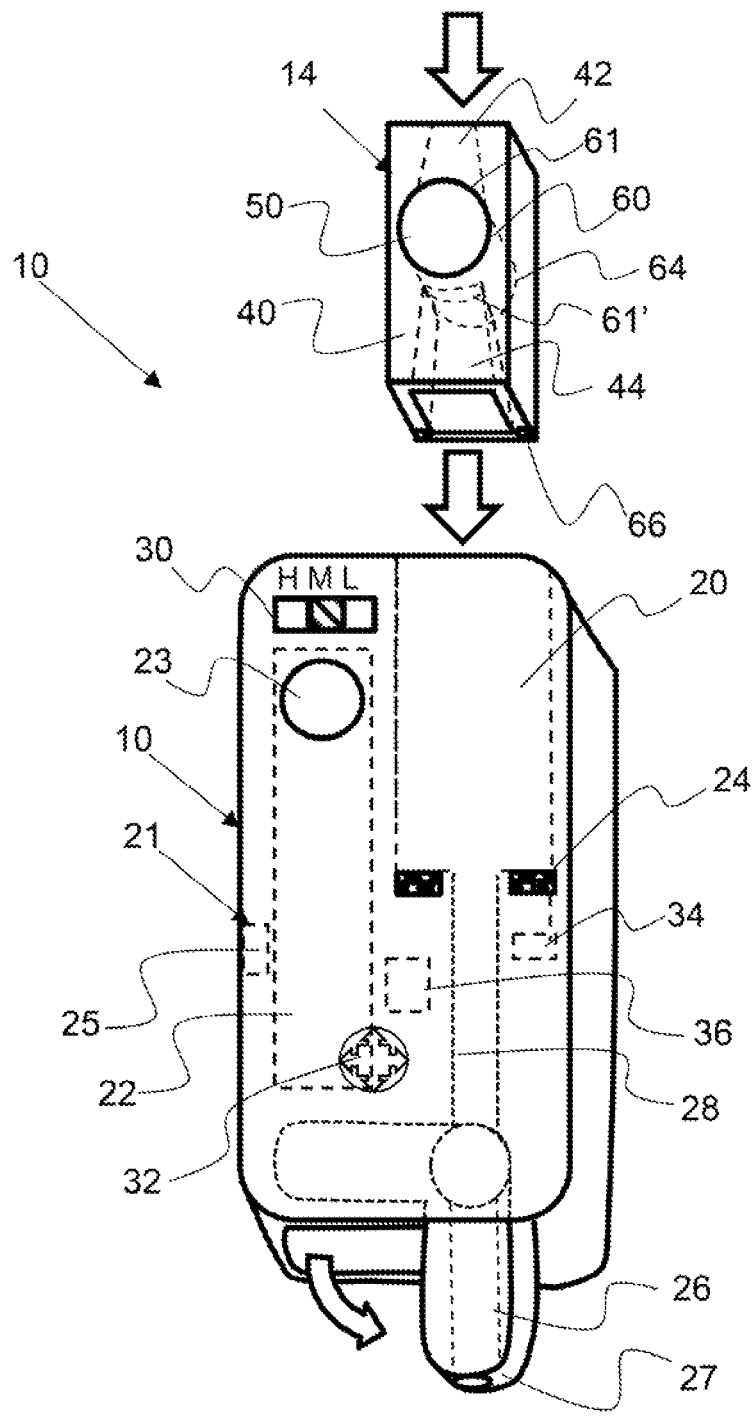

FIG. 1 shows a top down view of an exemplary vapor delivery device having a cartridge port configured to receive a detachable cartridge.

Figure 2:
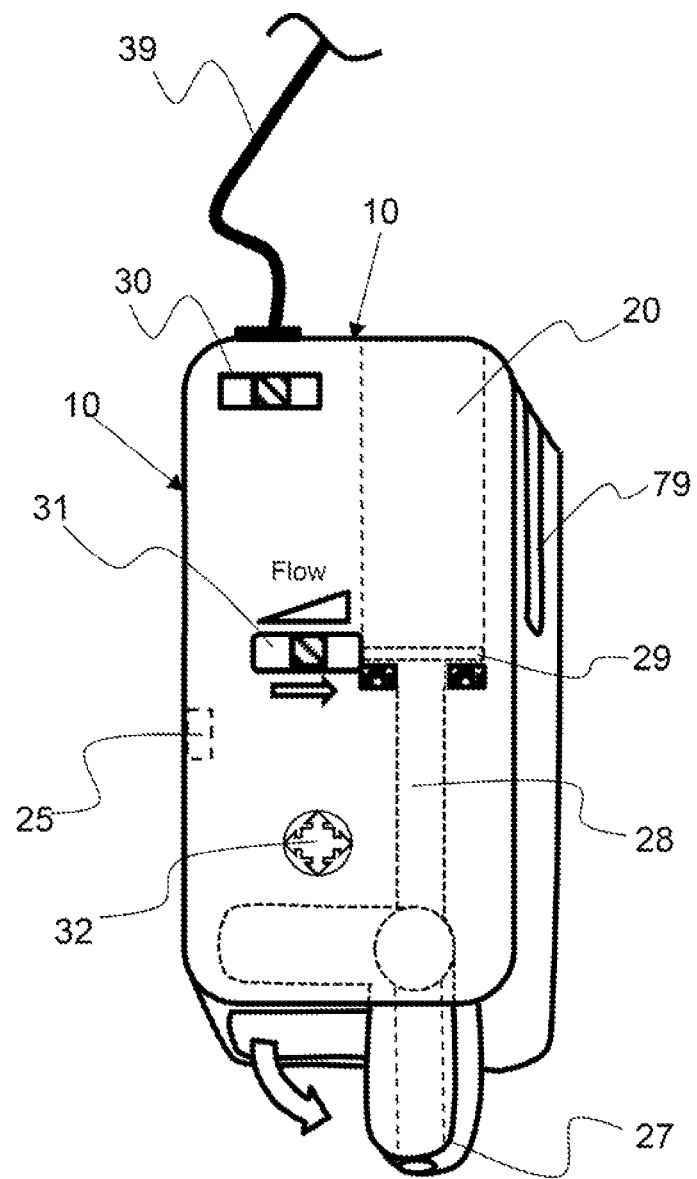

FIG. 2 shows a top down view of an exemplary vapor delivery device having an manipulator slot, a heat selector and a ready indicator.

Figure 3:
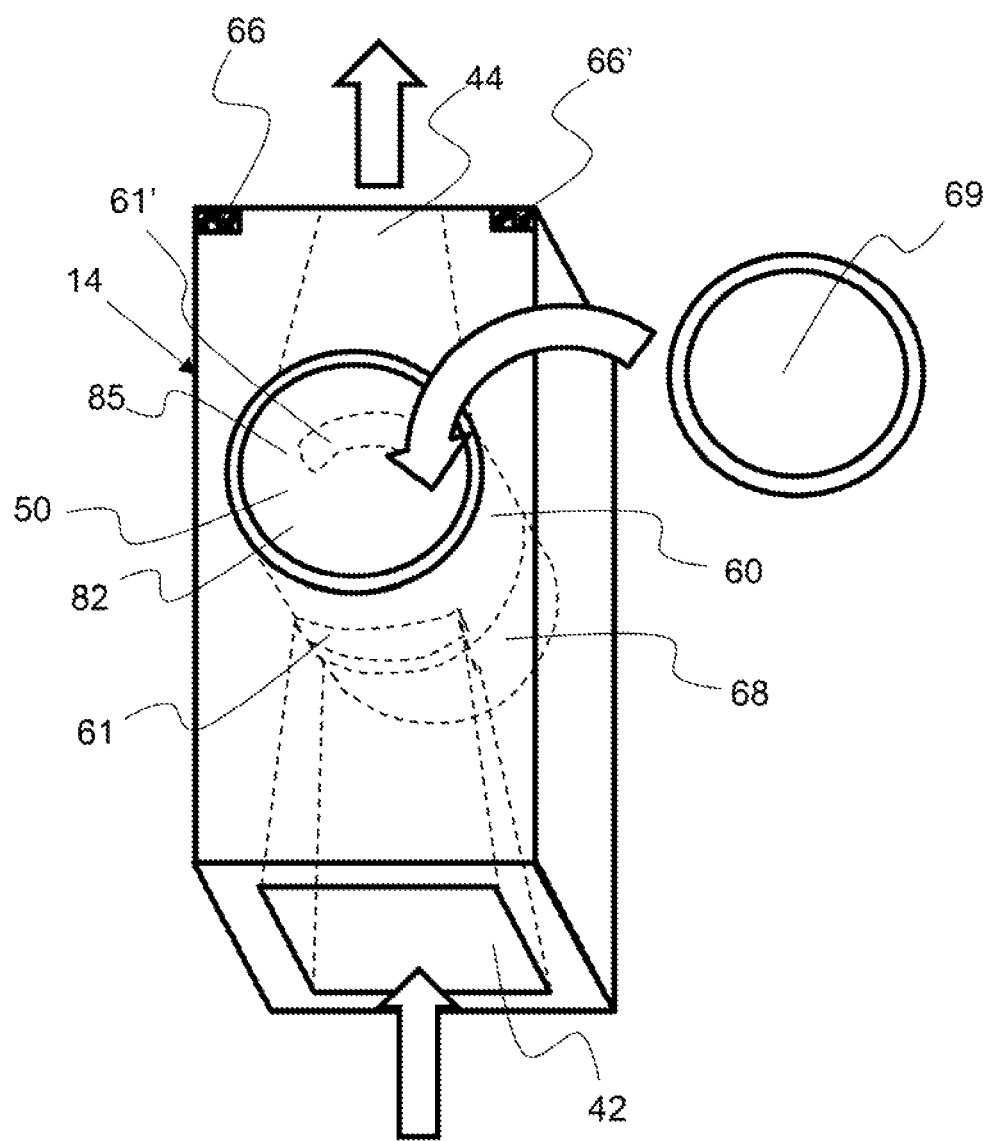

FIG. 3 shows a top down view of an exemplary detachable cartridge having a detachable oven closure.

Figures 4A, 4B:
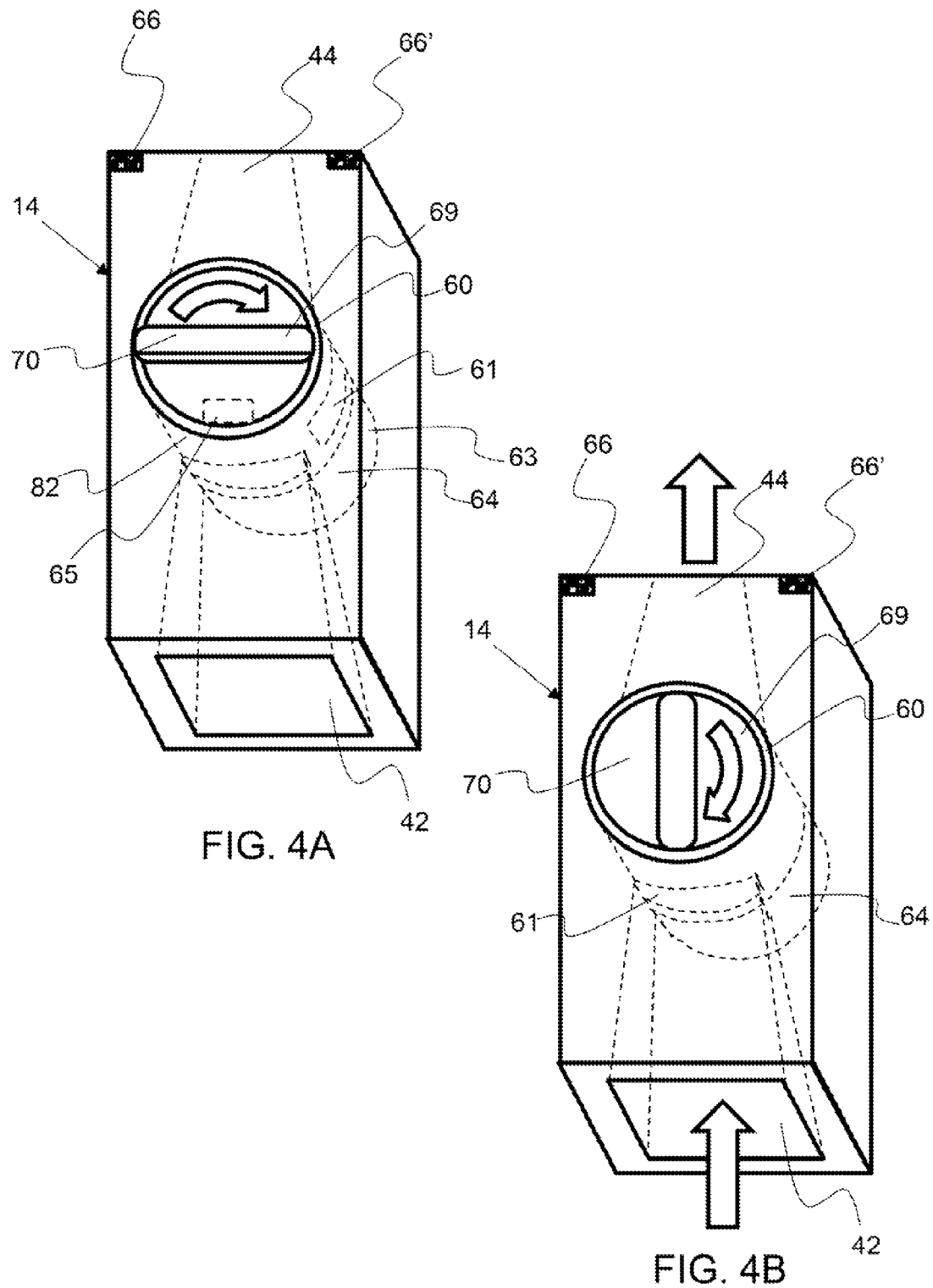

FIG. 4A shows a top down view of an exemplary detachable cartridge having an oven with an oven lever turned to prevent vapor produced in the interior of the oven from passing into the inlet and outlet airflow conduits.

FIG. 4B shows a top down view of an exemplary detachable cartridge having an oven with an oven lever turned to align the oven vent with the inlet and outlet airflow conduits, thereby allowing the vapor to be delivered to a user.

FIG. 5A shows an isometric view of an exemplary oven having first and second oven vents and a hinged oven closure.

FIG. 5B shows a top-down view of the exemplary oven shown in FIG. 5A with the oven closure in a down position over the oven access opening, wherein the oven closure comprises an oven lever that can be used to turn the oven within a detachable cartridge to align the oven vents with inlet and outlet airflow conduits.

Figure 6:
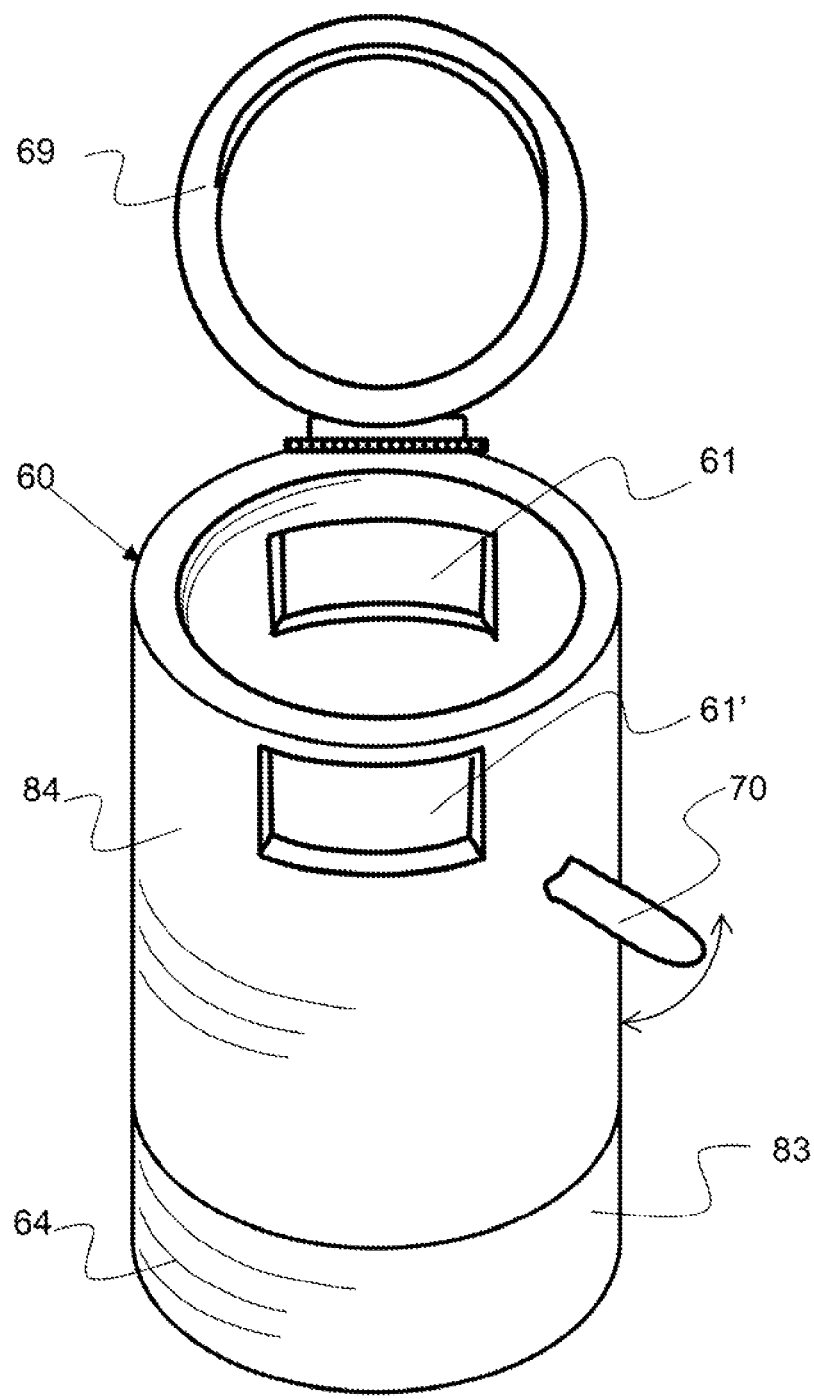

FIG. 6 shows an isometric view of an exemplary oven having first and second oven vents, a hinged oven closure and an oven lever extending from the exterior surface of the oven.

Figure 7:
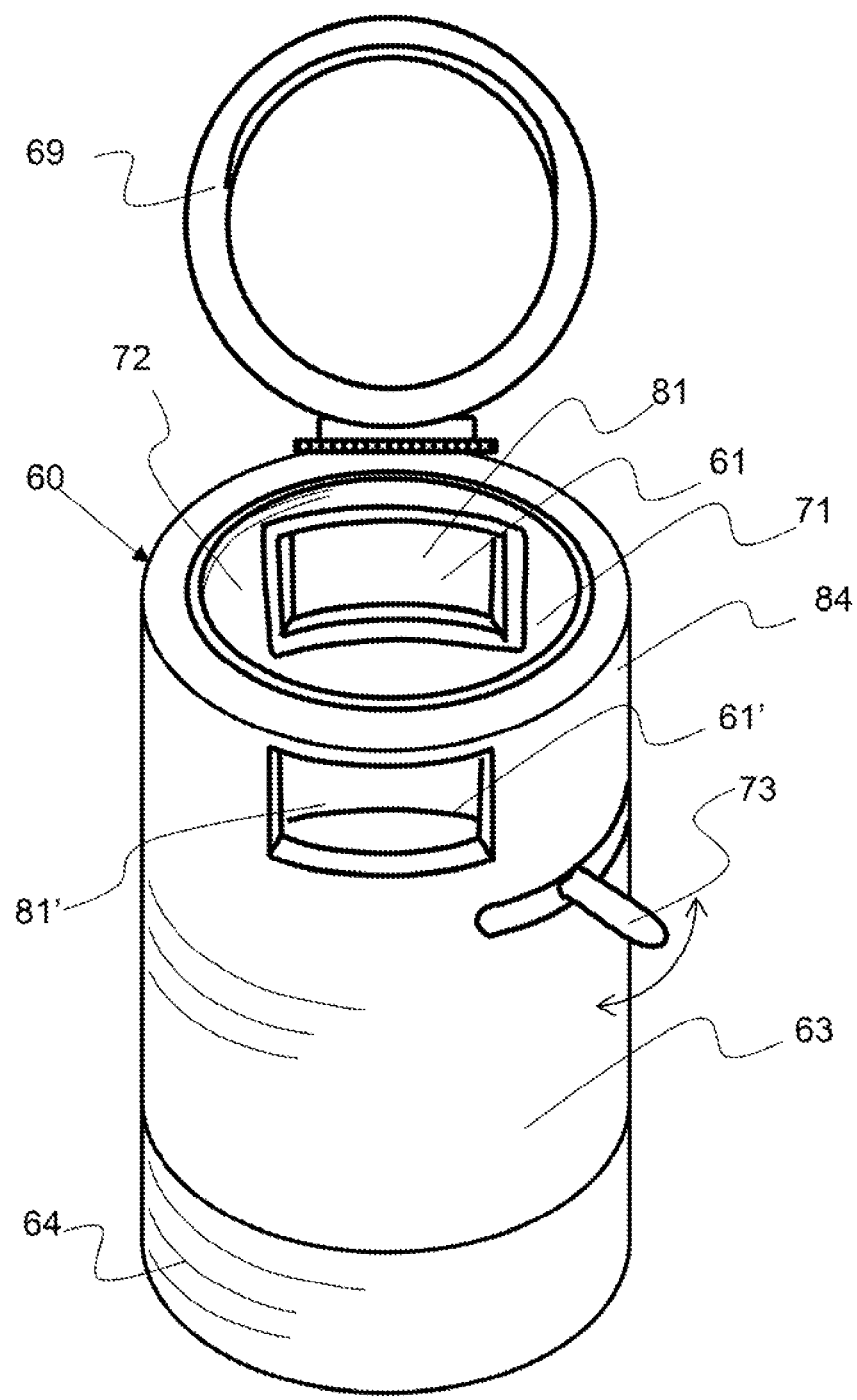

FIG. 7 shows an isometric view of an exemplary oven having first and second oven vents, a hinged oven closure, an oven vent damper configured on the interior surface of the oven and a damper manipulator extending out from the exterior of the oven through a slot within the oven wall.

Figure 8A:
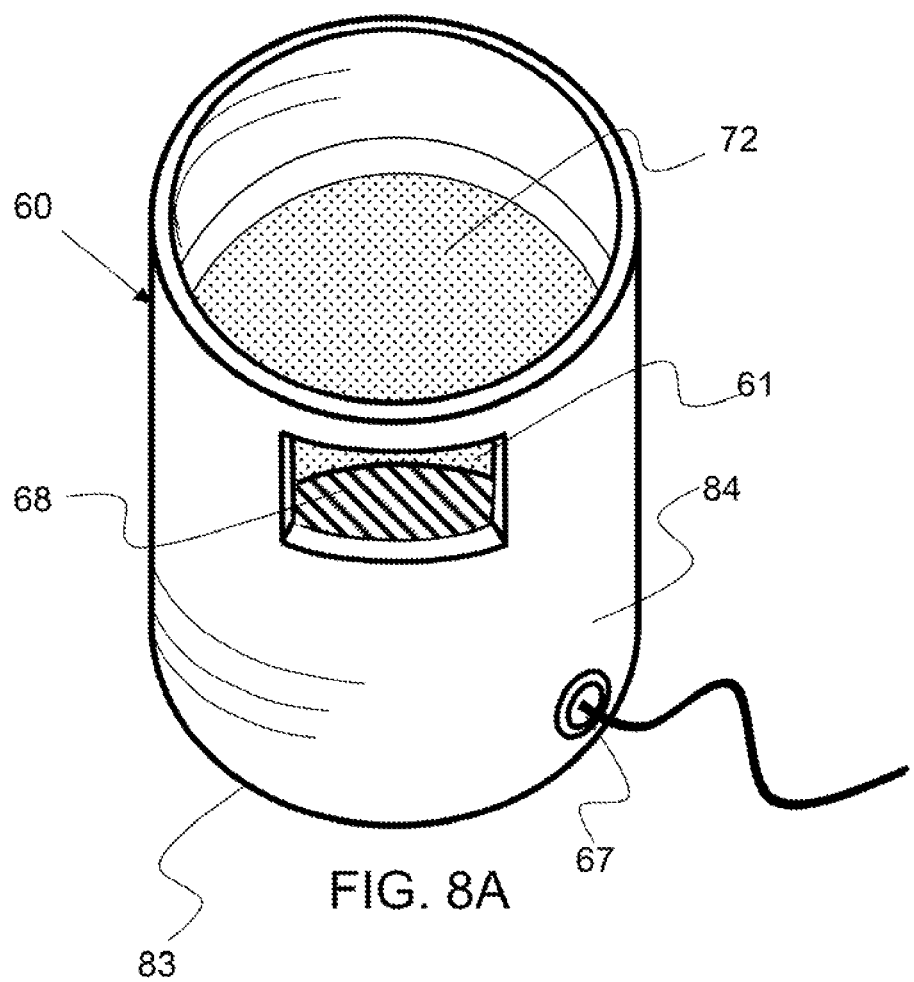

FIG. 8A shows an isometric view of an exemplary oven having a flexible heating element configured in the interior bottom of the oven, and an electrical coupling on the exterior surface of the oven.

Figure 8B:
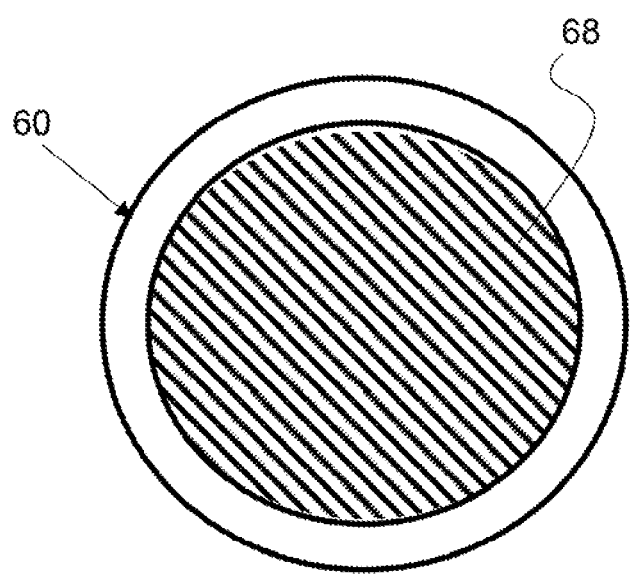

FIG. 8B shows a top-down view of the exemplary oven shown in FIG. 8A.

Figure 9A:
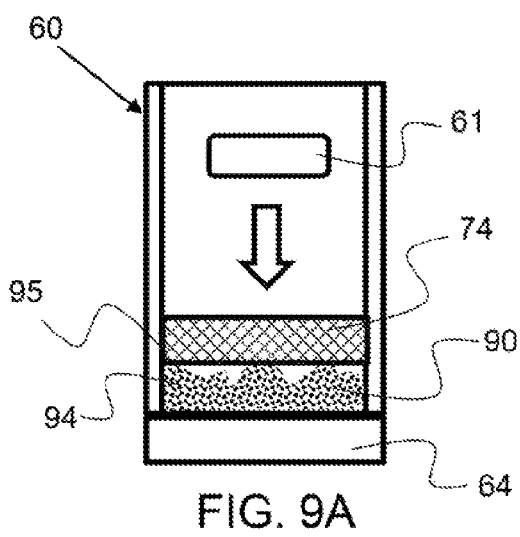

FIG. 9A shows a cross-sectional view of an exemplary oven having a plunger pressed down against vaporizable material.

Figure 9B:
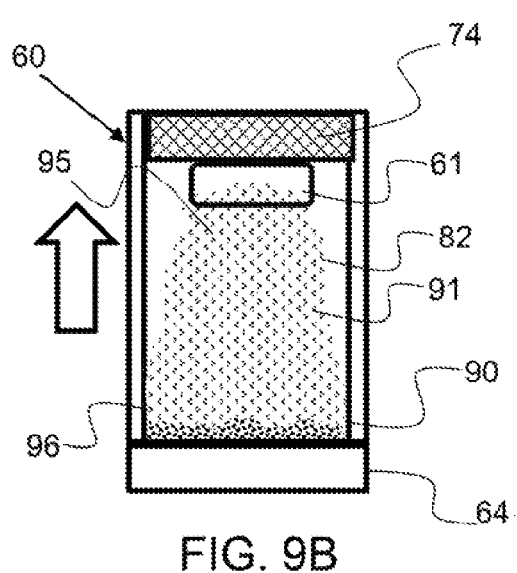

FIG. 9B shows a cross-sectional view of an exemplary oven having a plunger in an up position after the vaporizable material has been heated to produce a vapor and the vapor exiting the oven through the oven vent.

Figure 10:
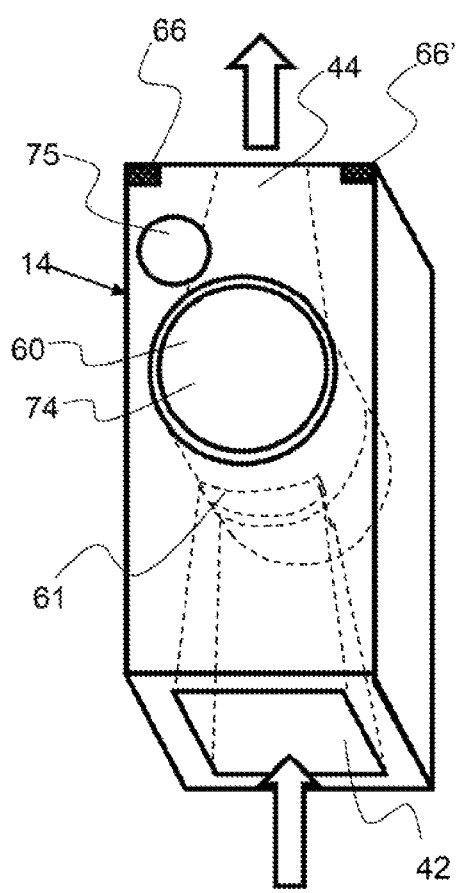

FIG. 10 shows a top-down isometric view of an exemplary detachable cartridge with a plunger type oven closure and a plunger release button.

Figure 11A:
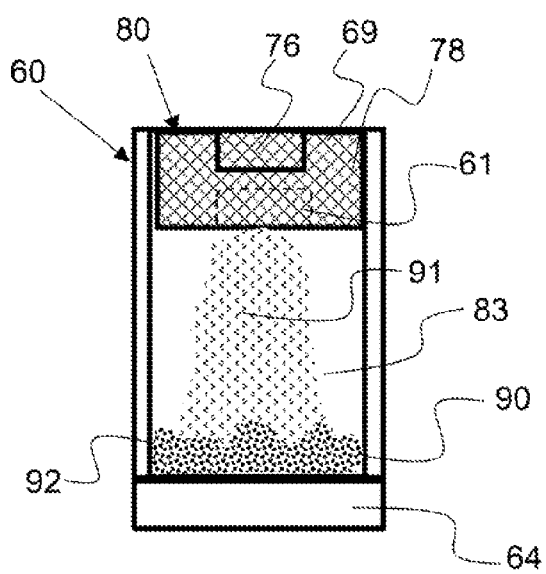

FIG. 11A shows a cross-sectional view of an exemplary oven having an oven closure that is configured with a tab in a vaporize (Vap) position whereby the oven closure vent openings are not aligned with the oven vents.

Figure 11B:
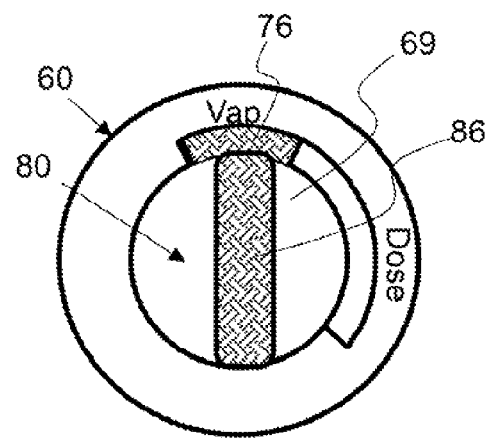

FIG. 11B show a top-down view of the exemplary oven shown in FIG. 11A with the oven closure tab in a Vap position.

Figure 12A:
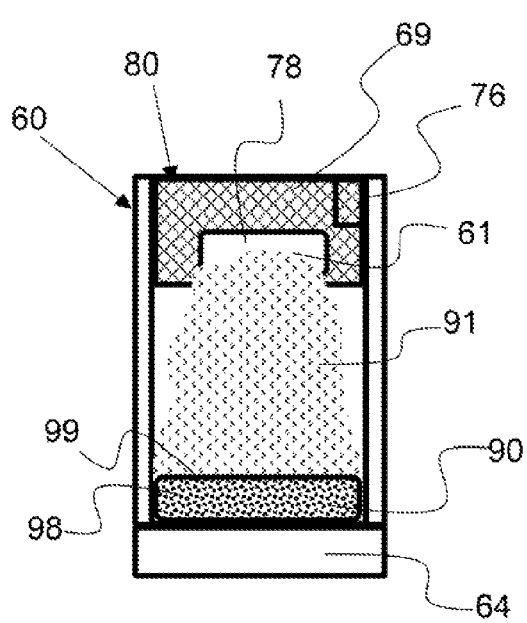

FIG. 12A show a cross-sectional view of an exemplary oven having an oven closure that is configured with a tab for locating the closure in dose position whereby the oven closure vent openings are aligned with the oven vents and vapor is exiting the oven through the oven vent.

Figure 12B:
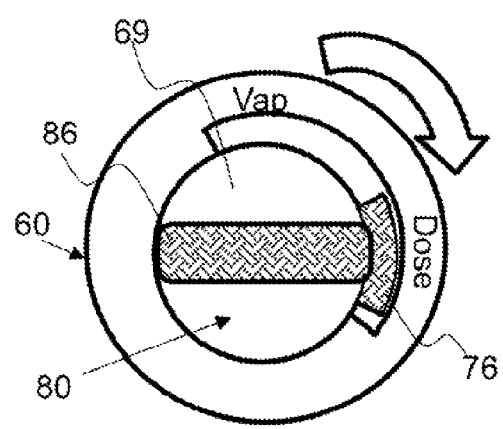

FIG. 12B show a top-down view of the exemplary oven shown in FIG. 12A with the oven closure tab in a dose position.

Figure 13:
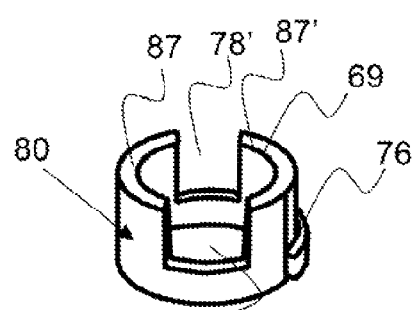

FIG. 13 shows an isometric view of an exemplary oven closure having a locating tab and two oven closure vent openings.

Figure 14:
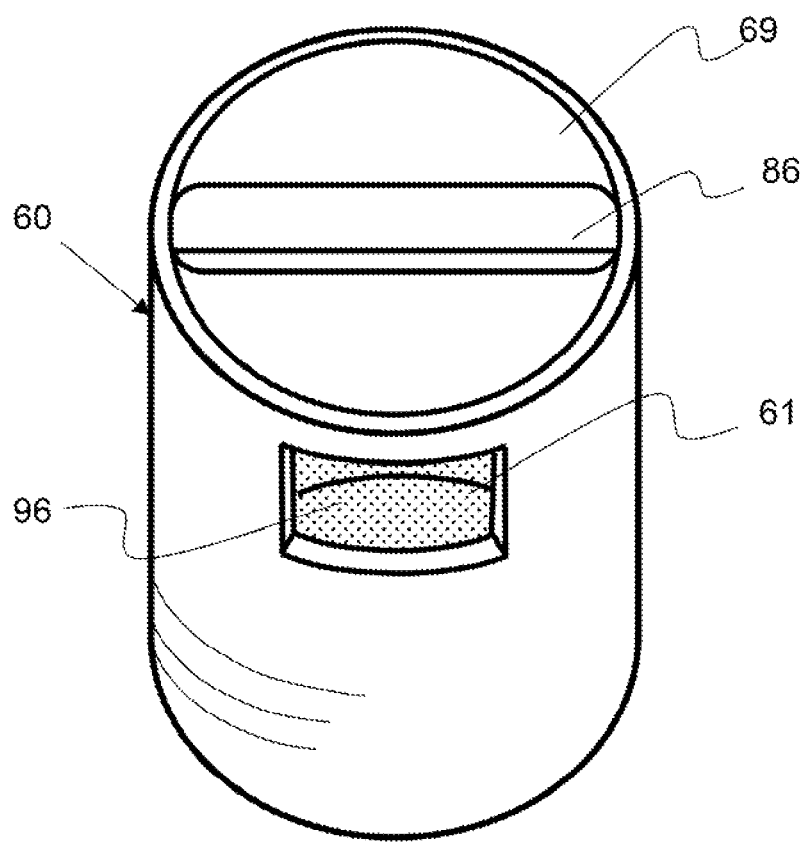

FIG. 14 shows an isometric view of an exemplary oven having an oven closure configured with an oven lever.

Figure 15:
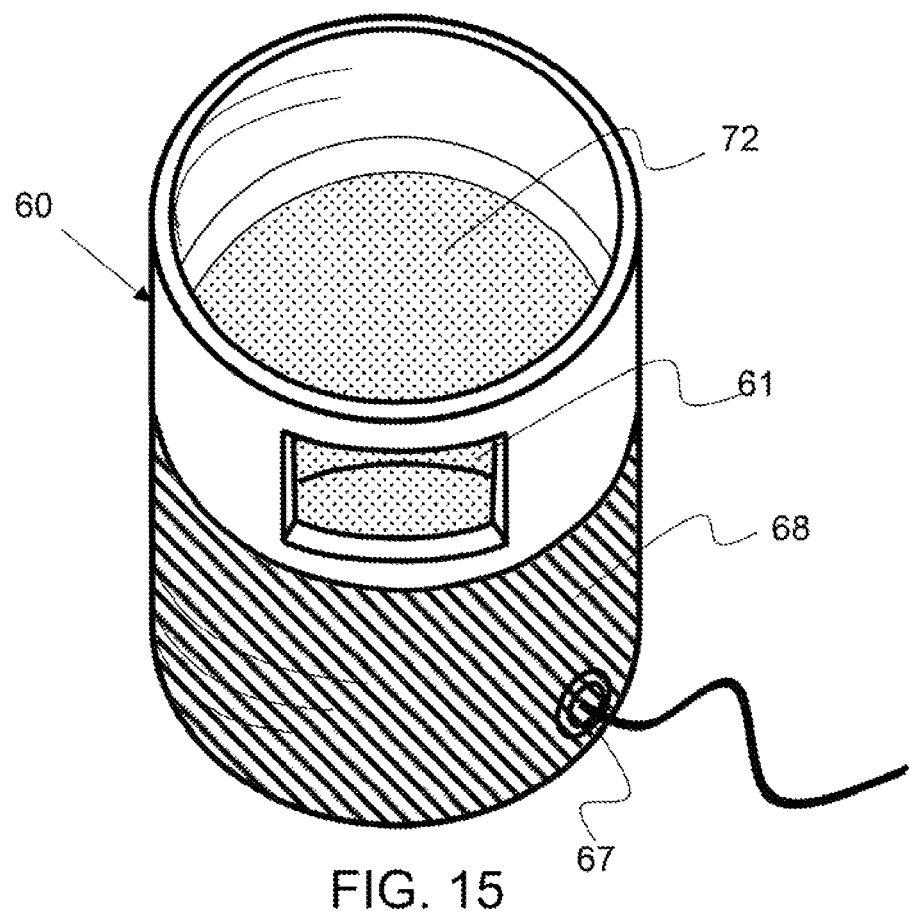

FIG. 15 shows an isometric view of an exemplary oven having a flexible heating element configured around the exterior of the oven.

Figure 16:
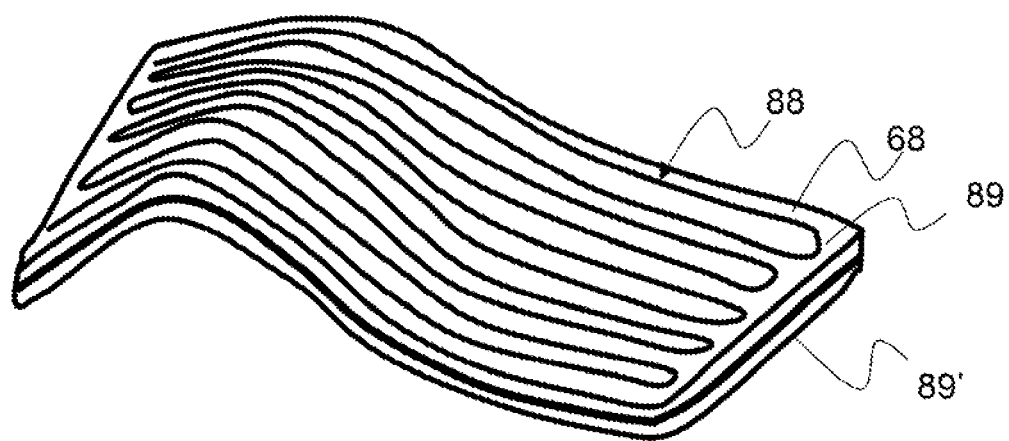

FIG. 16 shows an isometric view of an exemplary heating element.

Figure 17:
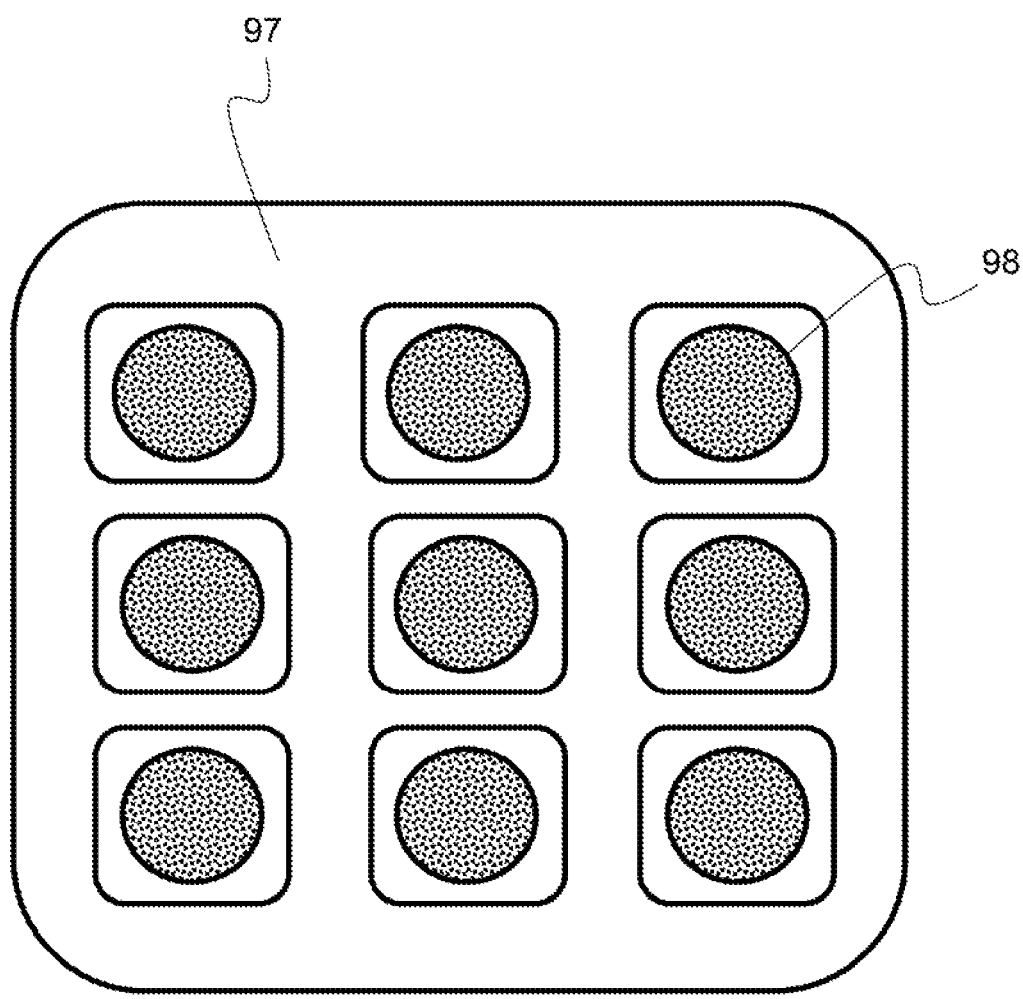

FIG. 17 shows a top view of an exemplary blister pack containing nine prepackaged doses.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

As shown in FIG. 1, an exemplary vapor delivery device 10 comprises a cartridge port 20 configured to receive a detachable cartridge 14. The detachable cartridge is configured to slide into the port, whereby the heating, element contacts 66 couple with the power supply contacts 24. The detachable cartridge comprises an inlet airflow conduit 42 and outlet airflow conduit 44 on either side of the oven 60. The oven is configured with vents 61, 61' that are aligned with the inlet and outlet airflow conduits as shown in FIG. 1. The outlet airflow conduit of the detachable cartridge aligns with a vapor conduit 28 that delivers the vapor to a mouthpiece 27 type delivery port 26. The mouthpiece 27 is configured to pivot out from the vapor delivery device body 21 as indicated by the arced arrow. A temperature sensor 34 measures the temperature or relative temperature of the heating element, and/or the oven or an oven surface, and when vaporizable material has been heated to an effective temperature for an effective duration of time to produce a vapor, the ready indicator 32 is activated. The ready indicator, as shown in FIG. 1 is a light that illuminates when a dose of vapor is ready. In an exemplary embodiment, a heat selector enables a user to set a high (H), medium (M), or low (L) heat set point. A controller 36, such as a microprocessor, controls the power supply to a heating element, receives input from the sensor and controls the ready indicator. A power supply 22, such as a rechargeable battery as shown, is configured in the vapor delivery device body 21, but may be configured in the detachable does cartridge. A charging port 25 may be used to recharge the batteries as needed.

As shown in FIG. 2, an exemplary vapor delivery device 10 has a manipulator slot 79, a heat selector 30 and a ready indicator 32. In one embodiment, the manipulator slot is configured to receive an oven or damper manipulator that is configured on the detachable cartridge. In another embodiment, a damper controller 31 is attached to a damper(s) 29 that is configured on the vapor delivery device body 21. In this embodiment, a damper controller is configured to either move the oven or to close at least one damper to the inlet or outlet airflow conduits. This damper 29 may be used to control the amount of airflow to and from an oven and the vaporizable material.

As shown in FIG. 3, an exemplary detachable cartridge 14 has a detachable oven closure 69, such as a lid. A user of the vapor delivery device may insert vaporizable material through the oven access opening 50 into the oven interior 82 and then close the oven 60 with the detachable oven closure 69. The oven comprises an interior volume 85. The interior volume may be any suitable size including, but not limited to, about 25 mm$^3$ or more, about 50 mm$^3$ or more, about 100 mm$^3$ or more, about 500 mm$^3$ or more, about 1 cc or more, about 10 cc or more and any range between and including the volumes provided. The cartridge may then be placed into the vapor delivery device body (not shown) to heat the vaporizable material to produce a vapor. The inlet and outlet airflow channels 42 and 44, respectively, are more clearly shown in FIG. 3. The inlet and outlet airflow channels are aligned with the vents 61, 61' of the oven 60. The bold arrows indicate the flow direction through the detachable cartridge. A detachable dose cartridge may be configured to be disposable, and may be sealed, whereby access to a dose of vaporizable material is prevented.

As shown in FIG. 4A, an exemplary detachable cartridge 14 has an oven 60 with an oven lever 70 turned to prevent vapor produced within the oven interior 82, or the interior volume of the oven, from passing, into the inlet and outlet airflow conduits 42, 44, respectively. The oven vent 61 is shown being substantially 90 degrees out of alignment with the inlet airflow channel 42. The oven closure 69 may be configured with a key or other mating portion 65 that locks the oven closure to the oven body 63. A oven closure may have a protrusion type mating portion that couples with a recess in the oven body, or vice versa. An oven closure locked radially in place with the oven body can then be used, by rotation of a oven lever, to rotate the oven body.

As shown in FIG. 4B, an exemplary detachable cartridge 14 has an oven 60 with an oven lever 70 turned to align the oven vents 61 with the inlet and outlet airflow conduits 42, 44, thereby allowing the vapor to be delivered to a user. A user would simply place the detachable cartridge into the cartridge port, turn the oven lever to the vaporize position, and when ready, turn the oven lever to the dose position, or a position to align the oven vents with the airflow conduits, as shown in FIG. 4B. It is to be noted that the oven 60 may be detachable from the cartridge. For example, an oven may be coupled to the detachable cartridge and the cartridge may then be placed into the cartridge port.

As shown in FIG. 5A, an exemplary oven 60 has first and second oven vents 61, 61', respectively, and a hinged oven closure 69. The oven shown is a detachable oven that may be removed and placed into a detachable cartridge. The hinged or otherwise attached oven closer 69 may prevent loss of the oven closure and may firmly secure the oven closure to the oven body 63, whereby the oven closure can be used to turn or rotate the oven when inserted into a detachable cartridge. A heating element 64 is configured in the base 83 of the oven 60. The heating element has a heating element contact 66 on the base to couple with a power supply contact configured with a detachable dose cartridge (not shown).

As shown in FIG. 5B, the exemplary oven 60 shown in FIG. 5A comprises an oven closure 69 having an oven lever 70 that can be used to turn the oven within a detachable cartridge. Indicators, such as Vap and Dose may be configured on the detachable cartridge to provide an indication of the proper orientation of the oven in the cartridge. An oven lever may be used to partially align the oven vents with airflow conduits, thereby allowing for damping the airflow as desired.

As shown in FIG. 6, an exemplary oven 60 has first and second oven vents 61, 61', a hinged oven closure 69 and an oven lever 70 extending from the exterior surface 84 of the oven. The oven lever may be configured to slide through a manipulator slot 79, as shown in FIG. 2 when the detachable dose cartridge, with the oven coupled thereto, is attached to the cartridge port. A heating element 64 is configured in the base 83 of the oven.

As shown in FIG. 7, an exemplary oven 60 has first and second oven vents 61, 61', a hinged oven closure 69, and an oven vent damper 71 configured on the interior surface 72 of the oven. A damper manipulator 73 extends out from the exterior of the oven body 63 through a slot within the oven wall. The oven vent damper has openings 81, 81' that are aligned with the oven vents 61, 61'. When the oven is in a vaporizing mode, the damper manipulator can be slid along the slot to rotate the vent damper to close off the oven vents. The vent damper openings 81, 81' may be moved out of alignment with the oven vents, thereby substantially preventing vapor produced within the oven from escaping through the oven vents. It is to be understood that an oven vent damper may be configured on the exterior of the oven 84, thereby eliminating the need for the slot through the oven wall.

As shown in FIG. 8A, an exemplary oven 60 has a flexible heating element 68 configured in the interior bottom of the oven, and an electrical coupling 67 on the exterior surface 84 of the oven. A heating element may be configured in any suitable location in, on, or around an oven, within a detachable cartridge, or as part of the vapor delivery device body. It is desirable to reduce heat loss and therefore configuring the heating element in close proximity, if not in contact with, the vaporizable material is preferred.

As shown in FIG. 8B, the exemplary oven shown in FIG. 8A comprises a flexible heating element 68 in the bottom of the interior of the oven 60. The vaporizable material will come in direct contact with the heating element in this embodiment.

As shown in FIG. 9A, an exemplary oven 60 has a plunger 74 pressed down against vaporizable material 90, that is a resin 94. The plunger presses the resin 94 against the heating element 64, thereby reducing the vapor volume 95 around the resin and reducing heat loss. The plunger is configured well below the oven vent 61. A plunger may be an oven closure that is configured to be pressed down within the interior of the oven. A plunger may be spring loaded or simply be weighted to remain down against the vaporizable material.

As shown in FIG. 9B, an exemplary oven 60 has a plunger 74 in an up position, after the vaporizable material 90 has been heated to produce a vapor 91. The vapor volume 95 is much larger than the vapor volume show in FIG. 9A. The vapor is exiting the oven through the oven vent 61. The liquid type 96 vaporizable material 90 produced a vapor within the oven interior 82.

As shown in FIG. 10, an exemplary detachable cartridge has a plunger type 74 oven closure 60 and a plunger release button 75. The plunger release button may be pressed when a ready indicator is activated. The user may press the plunger release button and the plunger may then be automatically moved to a position to allow vapor to exit the interior of the oven. In another embodiment, a plunger is automatically released by a controller when an the vaporizable material has been heated to an effective temperature for an effective amount of time.

As shown in FIG. 11A, an exemplary oven 60 has an oven closure 69 that is configured with a tab 76 in a vaporize (Vap) position whereby the oven closure vent openings 78 are not aligned with the oven vents 61. The vapor 91 being produced by the organic material 92 type vaporizable material 90 is trapped within the oven enclosure, or oven interior 83.

As shown in the top-down view of the exemplary oven shown in FIG. 11A, as shown in FIG. 118, the oven closure tab 76 is in a Vap position. The oven may have indicators, Vap and Dose for example, to show the correct orientation of the oven closure during the operation of the vapor delivery device. The oven closure lever 86 may be used to turn the oven closure. The oven closure lever may also be used to dampen the flow as desired.

As shown in FIG. 12A, an exemplary oven 60 has an oven closure 69 that is configured with a tab 76 in a dose position, whereby the oven closure vent openings 78 are, aligned with the oven vents 61. This orientation allows the vapor 91 to exit the oven through the oven vent 61. The vaporizable material 90 shown in FIG. 12A is a prepackaged dose 98, such as a resin formed into a particular shape that is configured to fit within the oven interior. In another embodiment, a prepackaged dose 98 may contain a covering 99 or enclosure that is configured to degrade, burn, break or otherwise be compromised when exposed to the vaporizing temperatures with an oven, as described herein.

As shown in the top-down view of the exemplary oven of FIG. 12A, as shown in FIG. 12B, the oven closure tab 76 is in a dose position. The oven closure has been turned, as indicated by the large arced arrow, to align the oven closure vent openings with the oven vents.

As shown in FIG. 13, an exemplary oven closure 69 has an oven closure tab 76, two oven closure vent openings 78, 78' and two vent closure portions 87*m* 87'. The vent closure portions block the oven vents as shown in FIG. 11A. The oven closure vent openings are aligned with the oven vents as shown in FIG. 12A. It is to be noted that the damper oven closure 80 shown in FIGS. 11-13 may comprise a single vent closure portion and/or a single closure vent opening.

As shown in FIG. 14, an exemplary oven 60 has an oven closure 69 configured with an oven closure lever 86. The oven closure lever may be configured to turn the oven or only the oven closure within the oven. Any suitable combination of dampers or vent closures may be configured to enable a user to open the oven vents by turning an oven closure lever. The oven 60 shown in FIG. 14 may be sealed to prevent access to the vaporizable material contained within. The oven may be a disposable dose and a heating element may be contained within a detachable dose cartridge or the vapor delivery device body.

As shown in FIG. 15, an exemplary oven 60 has a flexible heating element 68 configured around the exterior of the oven. It is to be noted that a flexible heating element, as shown in FIG. 15, may alternatively be configured on the inside of the oven.

As shown in FIG. 16, a flexible heating element 68 comprises a resistive portion 88, such as a resistive wire, between high temperature polymer or non-electrically conducting and flexible layers 89, 89'. In an exemplary embodiment the non-electrically conducting and flexible layers are a high temperature polymer such as polyimide, fluoropolymer and the like.

As shown in FIG. 17, a blister pack 97 contains nine individual prepackaged doses 98 of vaporizable material. The prepackaged doses may be configured to fit within an oven, as described herein.

Definitions

A sealed detachable dose cartridge, or oven, comprises a dose of vaporizable material that is contained and inaccessible therein. The dose cartridge or oven does not contain a substantial opening to allow access to the vaporizable material, such as a lid or detachable closure. A sealed oven may be provided with a set dose of vaporizable material. A sealed detachable does cartridge or oven may comprise a vent or vents to allow the release of vapor with a vapor delivery device however.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:
1. A vapor delivery device for the delivery of a dose of vaporizable material comprising:
 a. a detachable dose cartridge comprising;
  an oven having an interior volume configured to contain said vaporizable material, and comprising;
   at least one oven vent;
   a heating element; and
   at least one heating element contact that is coupled with said heating element;
 b. a cartridge port configured to receive said detachable dose cartridge;
 c. a power supply;

d. power supply contacts configured to couple with said heating element contacts of said detachable dose cartridge; and e. a delivery port coupled with a vapor conduit configured for a user to inhale a vapor produced from said vaporizable material;

whereby when said detachable dose cartridge is inserted into said cartridge port, the power supply contacts couple with said heating element contacts to enable the heating element to be heated by said power supply wherein the detachable dose cartridge comprises an inlet airflow conduit and an outlet airflow conduit; and wherein the oven comprises an oven closure having an oven closure lever, whereby the oven can be rotated by said oven closure lever to align the at least one oven vent with one of the inlet or outlet airflow conduits.

2. The vapor delivery device for the delivery of a dose of vaporizable material of claim 1, wherein the at least one oven vent comprises a first oven vent and a second oven vent configured to align with said inlet airflow conduit and outlet airflow conduit respectively.

3. The vapor delivery device for the delivery of a dose of vaporizable material of claim 1, wherein the oven closure is configured to be detachably attached to an oven access opening.

4. The vapor delivery device for the delivery of a dose of vaporizable material of claim 1, wherein the oven comprises an oven vent damper having a vent damper opening.

5. The vapor delivery device for the delivery of a dose of vaporizable material of claim 1, wherein the heating element comprises a flexible circuit.

6. The vapor delivery device for the delivery of a dose of vaporizable material of claim 1, wherein the heating element is configured in a base of the oven.

7. The vapor delivery device for the delivery of a dose of vaporizable material of claim 1, wherein the detachable dose cartridge is a sealed cartridge whereby the vaporizable material cannot be removed.

8. The vapor delivery device for the delivery of a dose of vaporizable material of claim 1, wherein the oven is a detachable oven and is a sealed oven comprising a dose of vaporizable material whereby the vaporizable material cannot be removed.

9. The vapor delivery device for the delivery of a dose of vaporizable material of claim 1, wherein the detachable dose cartridge comprises an access cover, whereby to said dose of vaporizable material can be inserted into said dose cartridge.

10. The vapor delivery device for the delivery of a dose of vaporizable material of claim 1, wherein the dose of vaporizable material is a sealed prepackaged unit comprising a dose covering.

11. The vapor delivery device for the delivery of a dose of vaporizable material of claim 1, comprising a temperature sensor configured to determine the temperature of the detachable dose cartridge.

12. A vapor delivery device for the delivery of a dose of vaporizable material comprising:

a. a detachable dose cartridge comprising;

an oven having an interior volume configured to contain said vaporizable material comprising;
a first and a second oven vent;
an inlet airflow conduit;
an outlet airflow conduit;
a flexible heating element; and
at least one heating element contact that is coupled with said heating element;

b. a cartridge port configured to receive said detachable dose cartridge;

c. a power supply;

d. power supply contacts configured to couple with said heating element contacts of said detachable dose cartridge; and e. a delivery port coupled with a vapor conduit configured for a user to inhale a vapor produced from said vaporizable material;

whereby when said detachable dose cartridge is inserted into said cartridge port, the power supply contacts couple with said heating element contacts to enable the heating element to be heated by said power supply; and whereby said first and second oven vents are configured to be blocked by a damper coupled to a lever that enables the damper to be rotated with respect to the oven.

13. A vapor delivery device for the delivery of a dose of vaporizable material comprising:

a. a detachable dose cartridge comprising;

an oven having an interior volume configured to contain said vaporizable material, and comprising:
at least one oven vent;
a heating element; and
at least one heating element contact that is coupled with said heating element;

wherein the oven comprises an oven closure configured to be detachably attached to an oven access opening;

b. a cartridge port configured to receive said-detachable dose cartridge;

c. a power supply;

d. power supply contacts configured to couple with said heating element contacts of said detachable dose cartridge; and e. a delivery port coupled with a vapor conduit configured for a user to inhale a vapor produced from said vaporizable material;

whereby when said detachable dose cartridge is inserted into said cartridge port, the power supply contacts couple with said heating element contacts to enable the heating element to be heated by said power supply; and wherein the oven comprises a plunger inserted into the interior volume past the at least one oven vent, wherein a vapor volume of said interior volume can be adjusted by the position of said plunger.

14. The vapor delivery device for the delivery of a dose of vaporizable material of claim 13, further comprising a plunger release that is configured to disengage the plunger and bring the plunger above the at least one vent.

* * * * *